United States Patent
Yamabe et al.

(10) Patent No.: US 6,884,805 B2
(45) Date of Patent: Apr. 26, 2005

(54) POLYMORPH FORMS OF N-(2,3-DIMETHYL-5,6,7,8-TETRAHYDROFURO[2,3-B]QUINOLIN-4-YL)-2-(2-OXOPYRROLIDIN-1-YL)ACETAMIDE

(75) Inventors: Haruko Yamabe, Tokyo (JP); Takayuki Ishige, Tokyo (JP)

(73) Assignee: Mitsubishi Pharma Corporation, Osaka (JP)

( * ) Notice: Subject to any disclaimer, the term of this patent is extended or adjusted under 35 U.S.C. 154(b) by 0 days.

(21) Appl. No.: 10/475,047

(22) PCT Filed: Apr. 19, 2002

(86) PCT No.: PCT/JP02/03916
§ 371 (c)(1),
(2), (4) Date: Oct. 17, 2003

(87) PCT Pub. No.: WO02/085910
PCT Pub. Date: Oct. 31, 2002

(65) Prior Publication Data
US 2004/0122034 A1 Jun. 24, 2004

(30) Foreign Application Priority Data

Apr. 19, 2001 (JP) ........................................ 2001-121681
Apr. 19, 2001 (JP) ........................................ 2001-121682

(51) Int. Cl.[7] ................ A61K 31/4741; C07D 491/048
(52) U.S. Cl. ........................................ 514/291; 546/89
(58) Field of Search ............................. 514/291; 546/89

(56) References Cited

U.S. PATENT DOCUMENTS 5,397,785 A    3/1995   Ninomiya et al.

FOREIGN PATENT DOCUMENTS

EP     0 427 636 A2    5/1991

OTHER PUBLICATIONS

Haleblian et al., "Pharmaceutical Applications of Polymorphism," *Journal of Pharmaceutical Sciences*, 58 (8), 911–929 (1969).

*Primary Examiner*—Charanjit S. Aulakh
(74) *Attorney, Agent, or Firm*—Leydig, Voit & Mayer, Ltd.

(57) ABSTRACT

The invention relates to novel polymorph crystal forms A and B of N-(2,3-dimethyl-5,6,7,8-tetrahydrofuro[2,3-b]quinolin-4-yl)-2-(2-oxopyrrolidin-1-yl)acetamide:

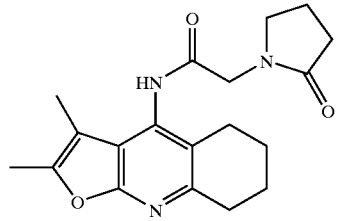

The compounds and pharmaceutical compositions thereof are useful for activating a malfunctioned cholinergic neuron that is associated with memory loss disturbances.

56 Claims, 5 Drawing Sheets

POLYMORPH FORMS OF N-(2,3-DIMETHYL-5,6,7,8-TETRAHYDROFURO[2,3-B]QUINOLIN-4-YL)-2-(2-OXOPYRROLIDIN-1-YL)ACETAMIDE

TECHNICAL FIELD

The invention relates to novel polymorph crystal forms of N-(2,3-dimethyl-5,6,7,8-tetrahydrofuro [2,3-b]quinolin-4-yl)-2-(2-oxopyrrolidin-1-yl) acetamide and activation of a malfunctioned cholinergic neuron therewith.

BACKGROUND ART

Many compounds are known to treat disturbances of memory that occur in certain biological disorders. For example, the memory loss in Alzheimer's disease or senile dementia is associated with a malfunction of a cholinergic neuron. Therapies pertaining to alleviating such memory loss include attempts to increase the acetylcholine content in the brain by using an anti-acetylcholinesterase (see, e.g., Japanese Patent Documents 61-148154, 63-141980, 63-225358, 63-238063, 63-239271, 63-284175, 63-297367, 64–73 and 1-132566, European Patent Application EP-A-268871, and International (PCT) Published Application WO 88/02256).

U.S. Pat. No. 5,397,785 discloses a class of 4-acylaminopyridine derivatives that activate malfunctioned cholinergic neurons. Compounds and acid addition salts thereof disclosed in the '785 patent are believed to improve disturbances of memory by a different mechanism than conventional compounds known to have anti-acetylcholinesterase activity. However, of all the compounds disclosed therein, the '785 patent provides no discussion regarding polymorphs of any of the compounds.

The ability of a substance to crystallize with more than one crystal structure is known as polymorphism, and a particular crystal form is called a polymorph. Different polymorphs of the same compound can have quite different physical properties, such as shelf-life and solubility. Some of these differences in physical properties can lead to differences in efficacy.

Because of these differences, it is useful to know which particular polymorph or mixture of polymorphs is being used.

Unfortunately, the detection of various polymorph forms of a single drug substance is not always readily discernable. Moreover, once a specific polymorph is recognized and desired for its characteristics, researchers must discover how to prepare consistently pure quantities of the polymorph form. Methods of preparing pure forms of a polymorph are not trivial and can require intensive discovery efforts.

Therefore, a pure or essentially pure polymorph of a compound is desirable from the standpoint of being able to accurately characterize the physical properties and biological efficacy against certain disease states, such as, for example, a malfunctioned cholinergic neuron associated with memory loss. Moreover, methods that allow for the production of not just one pure polymorph, but two polymorphs of a compound, also are desirable. The invention provides such polymorph compounds and methods related thereto.

DISCLOSURE OF INVENTION

The invention relates to two novel pure or essentially pure crystal forms of N-(2,3-dimethyl-5,6,7,8-tetrahydrofuro[2,3-b]quinolin-4-yl)-2-(2-oxopyrrolidin-1-yl)acetamide of formula (I):

(hereinafter referred to as the form A crystal and the form B crystal).

The form A crystal is characterized by one or more of the following: (a) a melting point (extrapolated onset) obtained from a differential scanning calorimetry curve lower than 220° C., particularly a melting point (extrapolated onset) obtained from a differential scanning calorimetry curve of about 217.6° C., (b) a peak at X-ray diffraction angle, 2θ, of 9.8° (±0.2°), (c) the absence of a peak at X-ray diffraction angle, 2θ, of 7.3° (±0.2°), (d) a water solubility of lower than 0.5 mg/mL, particularly a water solubility of about 0.35 mg/mL, and (e) greater stability in storage than the form B crystal.

The form B crystal is characterized by one or more of the following: (a) a melting point (extrapolated onset) obtained from a differential scanning calorimetry curve higher than 220° C., particularly a melting point (extrapolated onset) obtained from a differential scanning calorimetry curve of about 222.6° C., (b) a peak at X-ray diffraction angle, 2θ, of 7.3° (±0.2°), (c) the absence of a peak at X-ray diffraction angles, 2θ, of 9.8° (±0.2°), (d) a water solubility of higher than 0.5 mg/mL, particularly a water solubility of about 0.73 mg/mL, and (e) a worse stability in storage than the form A crystal.

The invention also provides a pharmaceutical bulk comprising either the form A crystal or the form B crystal. Moreover, the invention provides a pharmaceutical composition comprising a pharmaceutically acceptable carrier and either the form A crystal or the form B crystal.

The compounds and pharmaceutical compositions thereof are useful for activating a malfunctioned cholinergic neuron that is associated with disturbances of memory loss in mammals, particularly a human. The invention provides for uses of the compounds and pharmaceutical compositions for that purpose.

The invention further provides methods of preparing pure or essentially pure quantities of the form A crystal and the form B crystal with good reproducibility using a physiologically compatible solvent.

BRIEF DESCRIPTION OF THE DRAWINGS

FIG. 1 shows powder X-ray diffraction curves of the form A crystal (FIG. 1-a) and the form B crystal (FIG. 1-b).

BEST MODE FOR CARRYING OUT THE INVENTION

This invention results in two kinds of a specific pure or essentially pure crystal form of the compound N-(2,3- dimethyl-5,6,7,8-tetrahydrofuro[2,3-b]quinolin-4-yl)-2-(2-oxopyrrolidin-1-yl)acetamide: the form A crystal and the form B crystal. The compound N-(2,3-dimethyl-5,6,7,8-tetrahydrofuro[2,3-b]quinolin-4-yl)-2-(2-oxopyrrolidin-1-yl)acetamide, which is represented by the following chemical formula (I):

(I)

is a known compound disclosed in U.S. Pat. No. 5,397,785 (the '785 patent). Particulars about its preparation and its physical properties are found in Example 25 in the '785 patent. However, this example provides only the melting point of the powder obtained by recrystallizing crude crystals from a chloroform-ethyl acetate mixture. The '785 patent provides no information about which preparations yield which form of crystals or whether the compound has polymorphs or not. Moreover, when it is applied to human bodies as a medicament, it is less preferable halogenated solvents such as chloroform are used during preparation.

It has been surprisingly found that the preparation of N-(2,3-dimethyl-5,6,7,8-tetrahydrofuro[2,3-b]quinolin-4-yl)-2-(2-oxopyrrolidin-1-yl)acetamide by the '785 patent method results in a mixture of several forms of crystals in a proportion that varies depending on the preparation conditions. Therefore, the existence of various polymorph forms is virtually impossible to discern based on the method in the '785 patent.

The form A crystal is characterized by one or more of the following: (a) a melting point (extrapolated onset) obtained from a differential scanning calorimetry curve lower than 220° C., desirably in the range of about 213–220° C., preferably in the range of about 215–220° C., more preferably in the range of about 216–218° C., most preferably about 218° C., and particularly about 217.6° C., (b) at least one peak in the X-ray diffraction spectrum at diffraction angle, 2θ, of 8.7°, 9.8°, 11.4°, 13.3°, 15.5°, 16.8°, and/or 17.6° (±0.2°, respectively), preferably at least one peak in the X-ray diffraction spectrum at diffraction angle, 2θ, of 9.8° (±0.2°), (c) the absence of a peak (taking into account baseline noise and variations among instruments) at X-ray diffraction angle, 2θ, of 7.3°, 9.3°, 11.9°, and/or 14.8° (±0.2°, respectively), (d) a water solubility (at 25° C.) of lower than 0.5 mg/mL, desirably in the range of about 0.1–0.5 mg/mL, preferably in the range of about 0.2–0.45 mg/mL, more preferably in the range of about 0.3–0.4 mg/mL, and particularly about 0.35 mg/mL, and (e) a better stability at room temperature (i.e., about 25° C.) and during storage (i.e., over time) than the form B crystal.

The form B crystal is characterized by one or more of the following: (a) a melting point (extrapolated onset) obtained from a differential scanning calorimetry curve higher than 220° C., desirably in the range of about 220–225° C., preferably in the range of about 221–224° C., more preferably in the range of about 222–223° C., most preferably about 223° C., and particularly about 222.6° C., (b) at least one peak in the X-ray diffraction spectrum at diffraction angle, 2θ, of 7.3°, 9.3°, 11.9°, 13.5°, 14.8°, 15.9°, 17.5°, and/or 18.6° (±0.2°, respectively), preferably at least one peak in the X-ray diffraction spectrum at diffraction angle, 2θ, of 7.3° (±0.2°), (c) the absence of a peak (taking into account baseline noise and variations among instruments) at X-ray diffraction angle, 2θ, of 8.7°, 9.8°, and/or 16.8° (±0.2°, respectively), (d) a water solubility (at 25° C.) of higher than 0.5 mg/mL, desirably in the range of about 0.5–1 mg/mL, preferably in the range of about 0.6–0.9 mg/mL, more preferably in the range of about 0.7–0.8 mg/mL, and particularly about 0.73 mg/mL, and (e) a worse stability at room temperature (i.e., about 25° C.) and during storage (i.e., over time) than the form A crystal.

The invention, therefore, provides a stable, pure or essentially pure, crystal form A or B, particularly of a pharmaceutical bulk of the compound, to ensure standardized quality and invariable efficacy. In other words, the invention provides pure crystal form A or B of a pharmaceutical bulk of the compound that can be prepared with good reproducibility by using a physiologically compatible solvent, such as, preferably, ethanol, water, or a mixture thereof. The use of chloroform is not required to prepare the polymorphs A and B. Therefore, the form A crystal and form B crystal are more useful as a pharmaceutical bulk or an active ingredient of a medicament than the known compound disclosed in Example 25 of U.S. Pat. No. 5,397,785 since less preferable halogenated solvents such as chloroform can be avoided during preparation.

The term "essentially pure" implies that either the form A crystal or the form B crystal contains less than 10 wt. % of the other polymorph form, preferably contains less than 5 wt. % of the other polymorph form. Ideally, the aforementioned percentages refer to any other polymorph form to the extent there may exist polymorph forms other than form A and form B as described herein.

The novel crystal forms of N-(2,3-dimethyl-5,6,7,8-tetrahydrofuro[2,3-b]quinolin-4-yl)-2-(2-oxopyrrolidin-1-yl)acetamide as described herein can be prepared by the following method. The form A crystal and the form B crystal can be obtained from a solution with the proper supersaturability of N-(2,3-dimethyl-5,6,7,8-tetrahydrofuro[2,3-b]quinolin-4-yl)-2-(2-oxopyrrolidin-1-yl)acetamide. The form A crystal can be prepared from such a solution where the supersaturability is less than about 5. The form B crystal can be prepared from such a solution if the supersaturability is more than about 20. The supersaturability can be calculated by the method described in Example 5.

The form A crystal can be prepared from a solution of N-(2,3-dimethyl-5,6,7,8-tetrahydrofuro[2,3-b]quinolin-4-yl)-2-(2-oxopyrrolidin-1-yl)acetamide by, for example, (a) recrystallizing slowly (the precise time frame depends on the scale of the reaction, from several hours to several days) and/or (b) convert form B crystals into form A crystals by stirring the suspension slowly (the precise time frame depends on scale of the reaction, from several hours to several days). The form B crystal can be prepared from a solution of N-(2,3-dimethyl-5,6,7,8-tetrahydrofuro[2,3-b] quinolin-4-yl)-2-(2-oxopyrrolidin-1-yl)acetamide by, for example, dissolving crude crystal in a solvent, with heating, followed by cooling to a temperature less than room temperature (i.e., less than 25° C).

The process of the preparation of the form A and form B crystals of N-(2,3-dimethyl-5,6,7,8-tetrahydrofuro[2,3-b] quinolin-4-yl)-2-(2-oxopyrrolidin-1-yl)acetamide can use solvents that are safe with respect to the human body (e.g., pharmaceutically, pharmacologically, and/or physiologically acceptable), such as water and/or solvents of which the permitted daily exposure ("PDE") are over 10 mg/day according to the "ICH Guideline for Residual Solvents Q3C," preferably water and/or Class 3 solvents in the "ICH Guideline for Residual Solvents Q3C" such as acetic acid, acetone, anisole, 1-butanol, 2-butanol, butyl acetate, tert-butyl methyl ether, cumene, dimethyl sulfoxide, ethanol, ethyl acetate, diethyl ether, ethyl formate, formic acid, heptane, isobuthyl acetate, isopropyl acetate, methyl acetate, 3-methyl-1-butanol, methyl ethyl ketone, methyl isobuthyl ketone, 2-methyl-1-propanol, pentane, 1-pentanol, 1-propanol, 2-propanol, and propyl acetate.

The invention further provides a pharmaceutical composition comprising a pharmaceutically acceptable (e.g., physiologically acceptable or pharmacologically compatible) carrier and the form A or form B crystal. Similarly, the invention provides a therapeutic agent (e.g., an anti-dementia agent) or medicament comprising the form A or form B crystal, especially for the treatment of the diseases, disorders, or conditions described herein.

The form A crystal and the form B crystal of the invention are able to activate a malfunctioned cholinergic neuron. The crystal forms of the invention (and pharmaceutical compositions thereof), therefore, are useful in a method of activating a malfunctioned cholinergic neuron in a mammal, particularly a human, with a disease. By activating the cholinergic neuron in a mammal (e.g., a human) with a compound or composition of the invention, the mammal's disease is effectively treated or prevented. Examples of diseases that involve a malfunctioned cholinergic neuron include senile dementia; dementia caused by Alzheimer's disease, Huntington's disease, Pick's disease, Down's syndrome or Parkinson's disease; tardive dyskinesia; myasthenia gravis; glaucoma; or somnipathy.

When the form A crystal or the form B crystal of the invention is used as a medicament, its route of administration is not particularly limited, i.e., any suitable administrative route can be utilized. Thus, it can be administered either orally or parenterally. The medicament of the invention can be administered to patients while remaining the aforesaid crystal form. However, it is preferably administered as a pharmaceutical composition containing the active ingredient and additives, which are pharmaceutically acceptable (e.g., pharmacologically compatible). Pharmaceutically acceptable carriers are well known. The choice of carrier will be determined, in part, both by the particular composition and by the particular method used to administer the composition. Accordingly, there are a wide variety of suitable formulations of the pharmaceutical compositions of the invention. Although more than one route can be used to administer a particular composition, a particular route can provide a more immediate and more effective reaction than another route.

Pharmaceutically acceptable additives can be employed, such as vehicles, disintegrators, disintegrating aids, binders, lubricants, coating agents, pigments, diluents, bases, dissolving agents, dissolving aids, isotonizing agents, pH regulators, stabilizers, propellants, and adhesives.

Examples of preparations suitable for oral administration include tablets, capsules, powders, fine granules, granules, solutions and syrups. Examples of preparations suitable for parenteral administration include injections, drops, ointments, creams, percutaneously absorbing agents, eye drops, ear drops, inhalants and suppositories. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. However, the form of the preparation of the pharmaceutical composition is not restricted to those recited herein.

Additive vehicles can be added the preparations suitable for oral administration. Suitable additives vehicles include glucose, lactose, D-mannitol, starch and crystalline cellulose; disintegrators or disintegrating aids such as carboxymethyl cellulose, starch and carboxymethyl cellulose calcium salt; binders such as hydroxypropyl cellulose, hydroxypropylmethyl cellulose, poly (vinyl pyrrolidone) and gelatin; lubricants such as magnesium stearate and talc; coating agents such as hydroxypropylmethyl cellulose, saccharose, polyethylene glycol and titanium oxide; and bases such as Vaseline, liquid paraffin, polyethylene glycol, gelatin, kaolin, glycerin, purified water and hard fat. Typical additives for preparations suitable for injections or eye drops include dissolving agents or dissolving aids that can constitute aqueous or dissolved-before-use injections such as distilled water for injection, physiological saline solutions and propylene glycol; isotonizing agents such as glucose, sodium chloride, D-mannitol and glycerin; pH regulators such as inorganic acids, organic acids, inorganic salts, and organic salts.

The dosage of the medicament of the invention should be appropriately increased or decreased depending on the disease, the purpose of the treatment (e.g., prevention or treatment), and the conditions of the patient such as age, weight, and symptoms. However, in general, the daily dosage for an adult patient by oral administration is about 0.05–500 mg per day. In general, the aforesaid dosage can be administered one time, several times everyday, or every several days.

The invention described herein also is described in Japanese Patent Application No. 121681/2001 and Japanese Patent Application No. 121682/2001, to which priority is claimed. The invention may be further understood by reference to the following references: Chaki et al., Bioorganic & Medical Chemistry Letters, 5(14), 1489–1494 (1995); Chaki et a., Bioorganic & Medical Chemistry Letters, 5(14), 1495–1500 (1995); Bessho et al., Arznein.Forsh./Drug Res., 46(I), 369–373 (1996); Murai et al., J. Neuron. Transm. [GenSect], 98, 1–13 (1994); and Akaike et al., Jpn. J. Pharmacol., 76, 219–222 (1998).

EXAMPLES

The following examples further illustrate the invention but, of course, should not be construed as in any way limiting its scope.

Example 15 of '785 Patent

Synthesis of 2-(2-oxopyrrolidin-1-yl)-N-(3-methyl-5,6,7,8-tetrahydrothieno[2,3-b]quinolin-4-yl) acetamide Into a suspension of 1.26 g of sodium hydride (60% content) in 15 ml of N-ethylpyrrolidone, was added 3.28 g of 4-amino-3-methyl-5,6,7,8-tetrahydrothieno[2,3-b] quinoline at room temperature. The mixture was heated to 50.degree. C. and stirred for 40 minutes. Thereafter, 4.72 g of methyl 2-oxo-1-pyrrolidine acetate was added dropwise to the mixture at 50.degree. C. over a period of 30 minutes. After the stirring at 50.degree. C. for 20 minutes, the mixture was cooled to 15.degree. C. and poured into 130 ml aqueous solution containing 13.5 g of ammonium chloride. After extraction of the solution with 100 ml of chloroform, the extract was dried over anhydrous sodium sulfate, followed by evaporation to dryness. The resultant product was added with ethyl acetate, pulverized and filtered. The crude crystals were recrystallized from chloroform-ethyl acetate to obtain 4.31 g of the titled compound having the melting point of 244.degree. to 246.degree. C.

Example 25 of '785 Patent

N-(2,3-dimethyl-5,6,7,8-tetrahydrofuro[2,3-b] quinolin-4-yl)-2-(2-oxopyrrolidin-1-yl)acetamide was synthesized in the same way as in Example 15. Melting Point (° C.): 213–215

Reference Example 1

Replication of Example 25 of U.S. Pat. No. 5,397,785

This example describes the replication of Example 25 of U.S. Pat. No. 5,397,785 to prepare N-(2,3-dimethyl-5,6,7,8-tetrahydrofuro[2,3-b]quinolin-4-yl)-2-(2-oxopyrrolidin-1-yl)acetamide.

N-(2,3-dimethyl-5,6,7,8-tetrahydrofuro[2,3-b]quinolin-4-yl)-2-(2-oxopyrrolidin-1-yl)acetamide was prepared in the same way as in Example 25 of U.S. Pat. No. 5,397,785 by recrystallizing crude crystals of the substance from a chloroform-ethyl acetate mixture. The melting point of the resultant substance was measured by a Yanagimoto Micro Melting Point Apparatus. In particular, the resultant substance was put between the glass plates of the apparatus, which were placed on the hot plate of the apparatus and then heated to determine the temperature at which the resultant substance melted. The melting point was determined to be 213–215° C. The preparations in the same way were repeated, however, the X-ray diffraction patterns of the resultant substances were not reproducible.

Example 1

Preparation of Form A Crystal Material

This example describes the preparation of the form A crystal of N-(2,3-dimethyl-5,6,7,8-tetrahydrofuro[2,3-b]quinolin-4-yl)-2-(2-oxopyrrolidin-1-yl)acetamide.

500 mg of N-(2,3-dimethyl-5,6,7,8-tetrahydrofuro[2,3-b]quinolin-4-yl)-2-(2-oxopyrrolidin-1-yl)acetamide prepared by the method disclosed in Example 25 of U.S. Pat. No. 5,397,785 were dissolved in a mixed solvent of 4 ml of ethanol and 5 ml of water by heating to 70° C. To the solution was added 6 ml of water, and the resulting mixture was stirred at room temperature for 2 hours. The resulting crystals were filtered, washed with water, and then dried, resulting in 440 mg of the form A crystals. The melting point was measured by the same method set forth in Reference Example 1 and determined to be 216–218° C.

Example 2

Preparation of Form B Crystal Material

This example describes the preparation of the form B crystal of N-(2,3-dimethyl-5,6,7,8-tetrahydrofuro [2,3-b]quinolin-4-yl)-2-(2-oxopyrrolidin-1-yl)acetamide.

8.8 kg of crude crystals of the compound prepared by the method disclosed in Example 25 of U.S. Pat. No. 5,397,785 were dissolved in 55.7 kg of ethanol with heating. Floating dust was removed by hot filtration, and then 87 L of water was added to the filtrate. After evaporation of the mixture to remove 27 L of the solvent under reduced pressure, 104 L of water was added, and the solution was left to stand overnight. The resulting crystals were filtrated off, washed with water, and then dried, resulting in 7.5 kg of the form B crystals. The melting point was measured by the same method set forth in Reference Example 1 and determined to be 221–224° C.

Example 3

Preparation of Single Crystal of Form A

This example describes the preparation of single crystal of the form A crystal. 11 mg of the form A crystal obtained in Example 1 was added with acetonitrile, and the mixture was left standing at room temperature for seven weeks to obtain a transparent and colorless single crystal (0.3 mm×0.05 mm×0.02 mm). The intensity of the resulting single crystal was measured by X-ray two axes diffractometer (SMART 1000, MoK α 50 kV, 40 mA), and then the structure was characterized according to the direct method by conducting the high precision structure analysis based on the full-matrix method of least squares.

Crystallographic data:

Formula: $C_{19}H_{23}N_3O_3$

Lattice constant: a 20.92(3) Å, b 4.805(6) Å, c 33.94(4) Å

Volume: 3413(7) Å$^3$

Space Group: Pna2$_1$

Z: 8

Dx: 1.403 g/cm$^3$

On the basis of the crystal structure, the powder pattern was simulated to confirm that the resulting single crystal was the form A crystal.

Example 4

Preparation of Single Crystal of Form B

This example describes the preparation of single crystal of the form B crystal. 1.5 mg of the form A crystal obtained in Example 1 was added with a mixed solvent of 100 µL of ethanol and 20 µL of propanol. The mixture was left standing in a refrigerator for a day to obtain a transparent and colorless single crystal (0.2 mm×0.08 mm×0.02 mm). The intensity of the resulting single crystal was measured by X-ray two axes diffractometer (SMART 1000, MoK α 50 kV, 40 mA ), and then the structure was characterized according to the direct method by conducting the high precision structure analysis based on the full-matrix method of least squares.

Crystallographic data:

Formula: $C_{19}H_{23}N_3O_3$

Lattice constant: a 4.751(5) Å, b 23.87(3) Å, c 15.52(2) Å

Volume: 1757(3) Å$^3$

Space Group: P 2$_1$/c

Z: 4

Dx: 1.291 g/cm$^3$

On the basis of the crystal structure, the powder pattern was simulated to confirm that the resulting single crystal was the form B crystal.

Example 5

Determination of Form A Crystal Supersaturability 0.5 g of crude crystal of N-(2,3-dimethyl-5,6,7,8-tetrahydrofuro[2,3-b]quinolin-4-yl)-2-(2-oxopyrrolidin-1-yl)acetamide prepared by the method disclosed in Example 25 of U.S. Pat. No. 5,397,785 were dissolved in 5 mL of methanol to reflux with heating, to which was added 3.3 mL of water and then left standing at room temperature overnight (21.5 hours). The crystals that formed were filtrated off, and any remaining liquid was evaporated under a reduced pressure at 40° C. for 2 hours, resulting in 0.17 g of the form A crystals.

The supersaturability of the form A crystals was calculated as follows: The supersaturability (calculation) is equal to the concentration of the dissolving N-(2,3-dimethyl-5,6,7,8-tetrahydrofuro[2,3-b]quinolin-4-yl)-2-(2-oxopyrrolidin-1-yl)acetamide divided by the solubility of N-(2,3-dimethyl-5,6,7,8-tetrahydrofuro[2,3-b]quinolin-4-yl)-2-(2-oxopyrrolidin-1-yl)acetamide under the condition of crystallization.

The concentration of the dissolving N-(2,3-dimethyl-5,6,7,8-tetrahydrofuro[2,3-b]quinolin-4-yl)-2-(2-oxopyrrolidin-1-yl)acetamide is equal to the weight of N-(2,3-dimethyl-5,6,7,8-tetrahydrofuro [2,3-b]quinolin-4-yl)-2-(2-oxopyrrolidin-1-yl)acetamide divided by the total volume of solvents of crystallization.

The solubility of N-(2,3-dimethyl-5,6,7,8-tetrahydrofuro[2,3-b]quinolin-4-yl)-2-(2-oxopyrrolidin-1-yl)acetamide under the condition of crystallization refers to the solubility of N-(2,3-dimethyl-5,6,7,8-tetrahydrofuro[2,3-b]quinolin-4-yl)-2-(2-oxopyrrolidin-1-yl)acetamide in the solvents used in crystallization at about room temperature.

Accordingly, the supersaturability of the form A crystals was calculated as follows:
Concentration of the dissolving N-(2,3-dimethyl-5,6,7,8-tetrahydrofuro[2,3-b]quinolin-4-yl)-2-(2-oxopyrrolidin-1-yl)acetamide=500 mg/(5 mL+3.3 mL)=60.24mg/mL Solubility of N-(2,3-dimethyl-5,6,7,8-tetrahydrofuro[2,3-b]quinolin-4-yl)-2-(2-oxopyrrolidin-1-yl)acetamide under the condition of crystallization (solubility of N-(2,3-dimethyl-5,6,7,8-tetrahydrofuro [2,3-b]quinolin-4-yl)-2-(2-oxopyrrolidin-1-yl)acetamide in 60% methanol used as the solvent of crystallization at about room temperature)=28.05 mg/mL
Supersaturability (calculation)=60.24 mg/mL/28.05 mg/mL=2.1

Example 6

Determination of Form B Crystal Supersaturability 0.5 g of crude crystal of N-(2,3-dimethyl-5,6,7,8-tetrahydrofuro[2,3-b]quinolin-4-yl)-2-(2-oxopyrrolidin-1-yl)acetamide prepared by the method disclosed in Example 25 of U.S. Pat. No. 5,397,785 were dissolved in 5 mL of methanol to reflux with heating, to which was added 45 mL of water and then left standing at room temperature for 2.5 hours. The crystals that formed were filtrated off, and any remaining liquid was evaporated under reduced pressure at 40° C. for 2 hours, resulting in 0.4 g of the form B crystals.

The supersaturability of the form B crystals was calculated in the same manner as set forth in Example 5.
Concentration of the dissolving N-(2,3-dimethyl-5,6,7,8-tetrahydrofuro[2,3-b]quinolin-4-yl)-2-(2-oxopyrrolidin-1-yl)acetamide=500 mg/(5 mL+45 mL)=10 mg/mL Solubility of N-(2,3-dimethyl-5,6,7,8-tetrahydrofuro[2,3-b]quinolin-4-yl)-2-(2-oxopyrrolidin-1-yl)acetamide under the condition of crystallization (solubility of N-(2,3-dimethyl-5,6,7,8-tetrahydrofuro[2,3-b]quinolin-4-yl)-2-(2-oxopyrrolidin-1-yl)acetamide in 10% methanol used as the solvent of crystallization at about room temperature)=0.41 mg/mL
Supersaturability (calculation)=10 mg/mL/0.41 mg/mL= 24.4

Example 7

Conversion of Form B Crystal to Form A Crystal

A suspension was prepared by adding 0.5 g of form B crystals of N-(2,3-dimethyl-5,6,7,8-tetrahydrofuro [2,3-b]quinolin-4-yl)-2-(2-oxopyrrolidin-1-yl)acetamide to 10 mL of water. The suspension was stirred for 24 hours, and then the filtrating off resulted in the form A crystals. The powder X-ray diffraction pattern of the resulting crystals was measured to confirm that the resulting crystals were form A crystals.

Example 8

Form A and Form B Crystal Characteristics

Figure 1A:
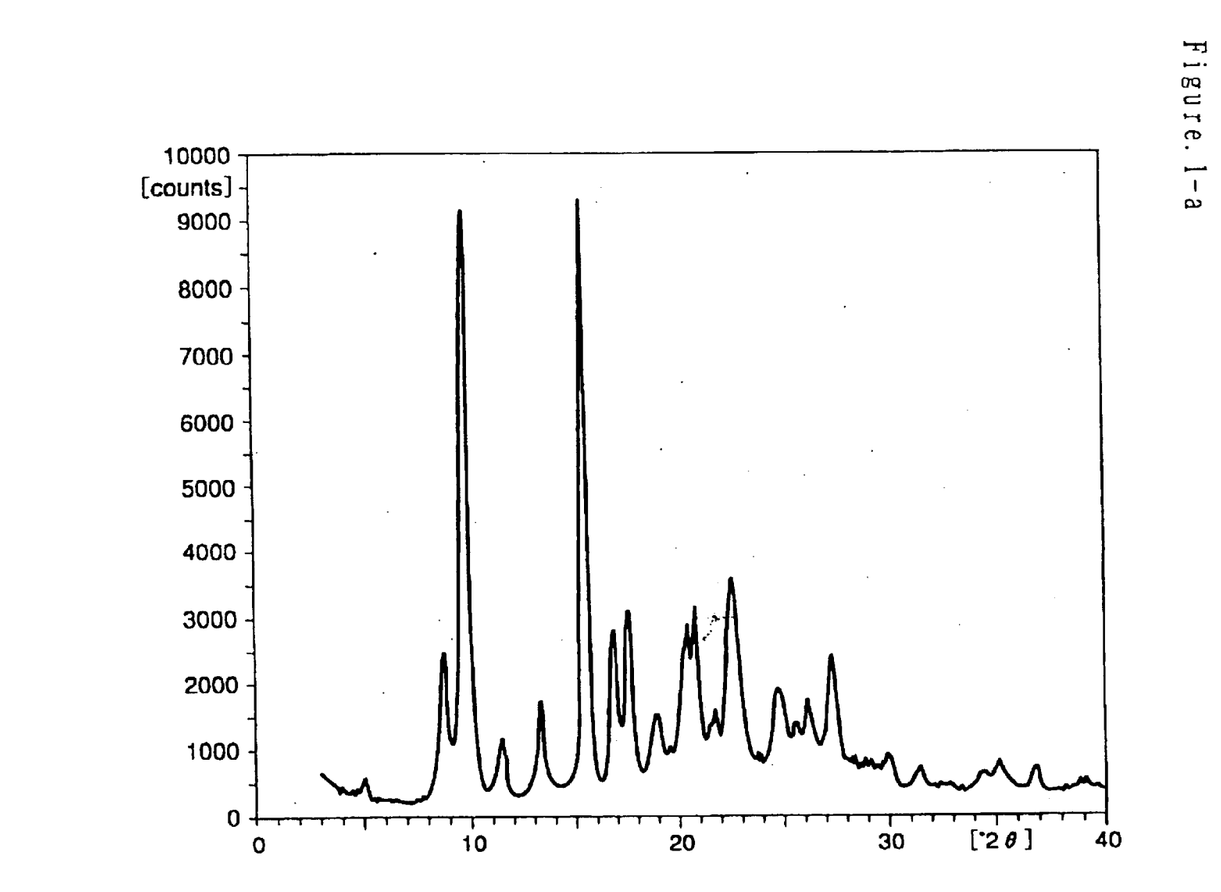
Figure 1B:
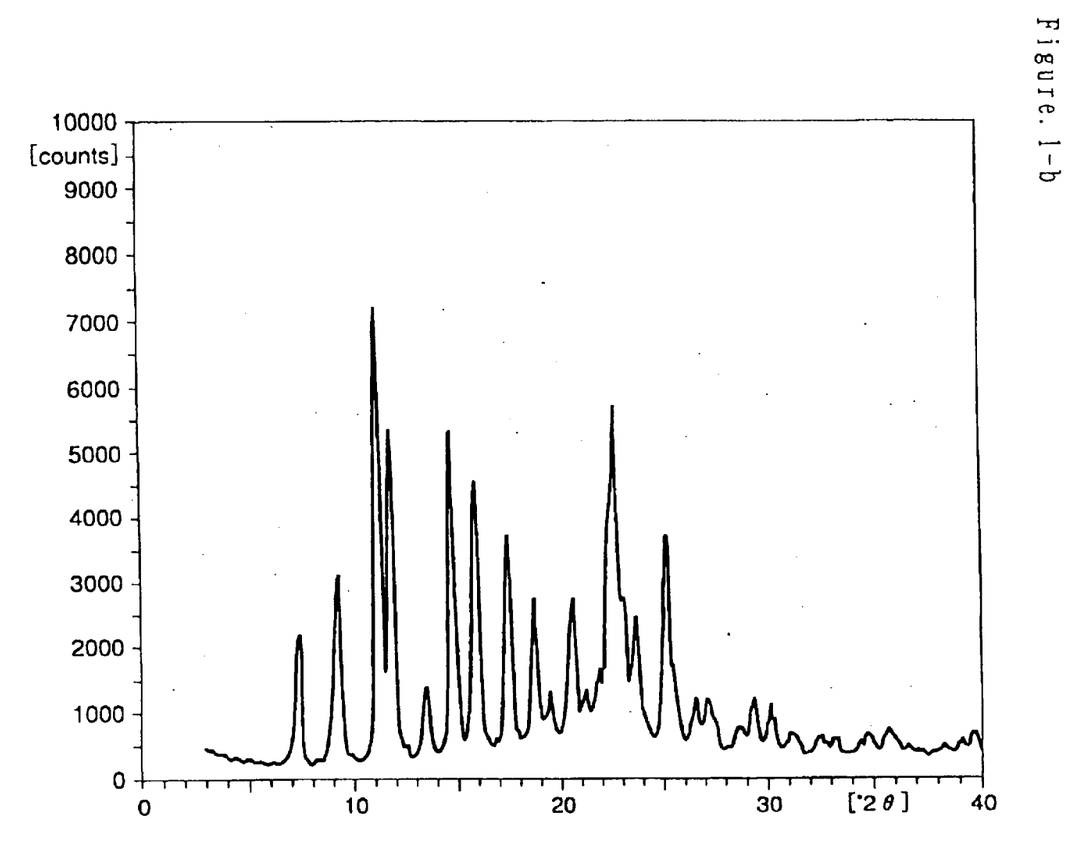

This example describes the characteristics of crystal forms A and B.
(1) Powder X-ray Diffraction Analysis (XRD)
The powder X-ray diffraction patterns of the form A crystal and the form B crystal were measured under the following conditions:
Diffractometer: PHILIPS PW1700
Target: Cu
Monochro.: Graphite
Tube Voltage: 40 kV
Tube Current: 30 mA
Divergence Slit: 1°
Receiving Slit: 0.2 mm
Scatter Slit: 1°
Range: 3–40° 2θ
The powder X-ray diffraction patterns of the form A crystal and the form B crystal are shown in FIG. 1. The pattern of the form A is shown in FIG. 1-a and the pattern of the form B is shown in FIG. 1-b.

The most characteristic peak of the form A crystal is that appearing at diffraction angles, 2θ, of 9.8° (±0.2°). The particularly characteristic peaks of the form A crystal are those appearing at diffraction angles, 2θ, of 8.7°, 9.8°, and 16.8° (±0.2°, respectively). The characteristic peaks of the form A crystal are those appearing at diffraction angles, 2θ, of 8.7°, 9.8°, 11.4°, 13.3°, 15.5°, and 16.8° (±0.2°, respectively). The main peaks are those appearing at diffraction angles, 2θ, of 8.7°, 9.8°, 11.4°, 13.3°, 15.5°, 16.8°, and 17.6° (±0.2°, respectively). All of the peaks are those appearing at diffraction angles, 2θ, of 5.1°, 8.7°, 9.8°, 11.4°, 13.3°, 15.5°, 16.8°, 17.6°, and 18.9° (±+0.2°, respectively).

Figure 2:
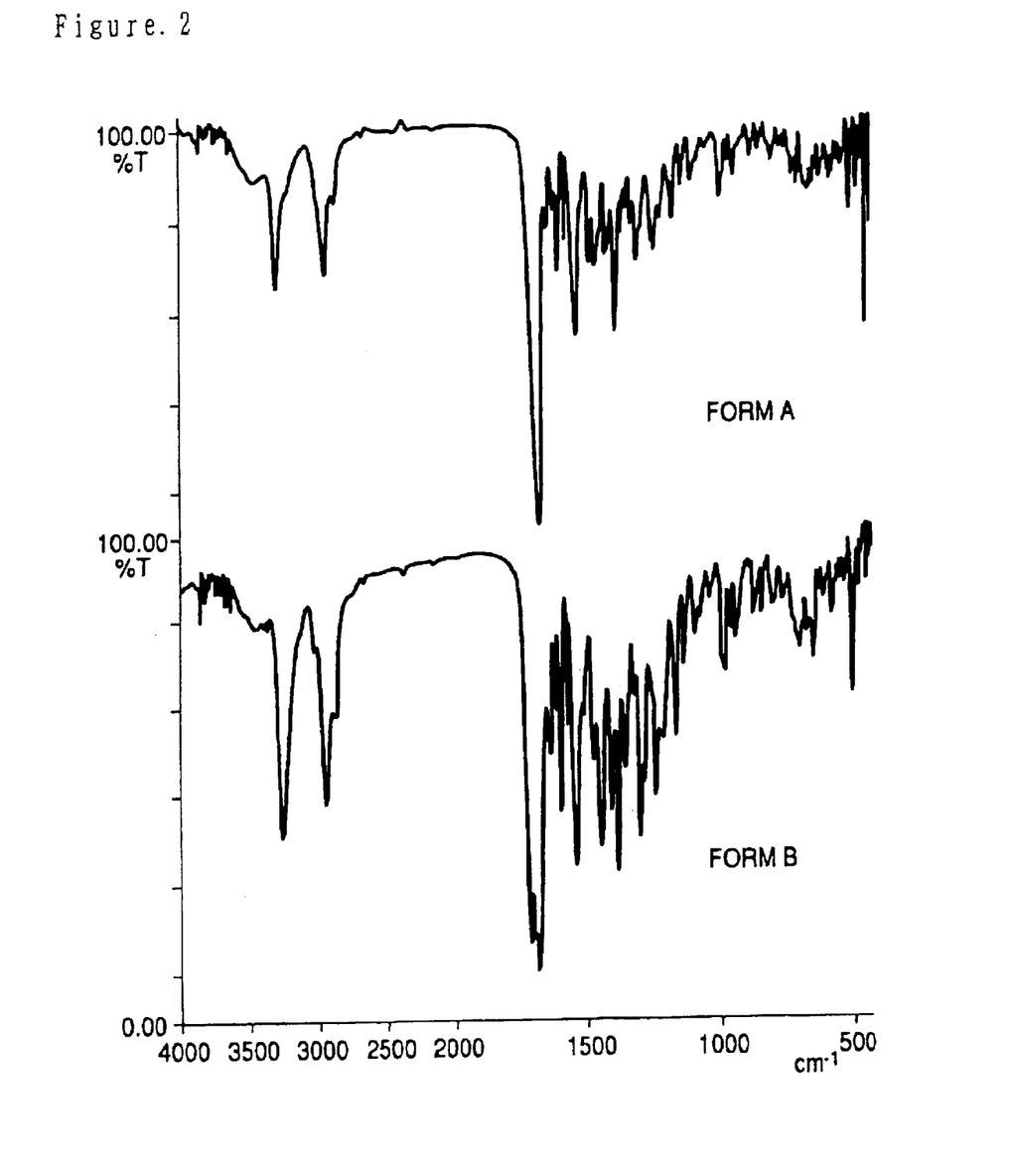
FIG. 2 shows infrared (IR) absorption spectroscopy patterns of the form A crystal and the form B crystal.

The most characteristic peak of the form B crystal is that appearing at diffraction angles, 2θ, of 7.3° (±0.2°). The particularly characteristic peaks of the form A crystal are those appearing at diffraction angles, 2θ, of 7.3°, 9.3°, and 11.9° (±0.2°, respectively). The characteristic peaks of the form B crystal are those appearing at diffraction angles, 2θ, of 7.3°, 9.3°, 11.9°, and 14.8° (±0.2°, respectively). The main peaks are those appearing at diffraction angles, 2θ, of 7.3°, 9.3°, 11.9°, 13.5°, 14.8°, 15.9°, 17.5°, and 18.6° (±0.2°, respectively). All of the peaks are those appearing at diffraction angles, 2θ, of 7.3°, 9.3°, 11.3°, 11.9°, 13.5°, 14.8°, 15.9°, 17.5°, 18.6°, and 19.4° (±0.2°, respectively).
(2) Infrared Absorption Spectroscopy Analysis (IR)
The infrared absorption spectroscopy patterns of the form A crystal and the form B crystal were measured using KBr pellets under the following conditions:
Infrared spectrometer: Paragon 1000 FTIR (Perkin-Elmer)
Sensitivity: 2.0 cm$^{-1}$
Range: 4000–400 cm$^{-1}$
The infrared absorption spectroscopy patterns of the form A crystal and the form B crystal are shown in FIG. 2.
(3) Differential Scanning Calorimetry Analysis (DSC)
Each sample (2 mg each) of the form A crystal and the form B crystal was placed on a differential scanning calorimetry meter DSC6200R (Seiko Instruments), and the measurement was performed with a heating rate of 20° C./minute (40–250° C., $N_2$ 40 ml/minute).

Figure 3:
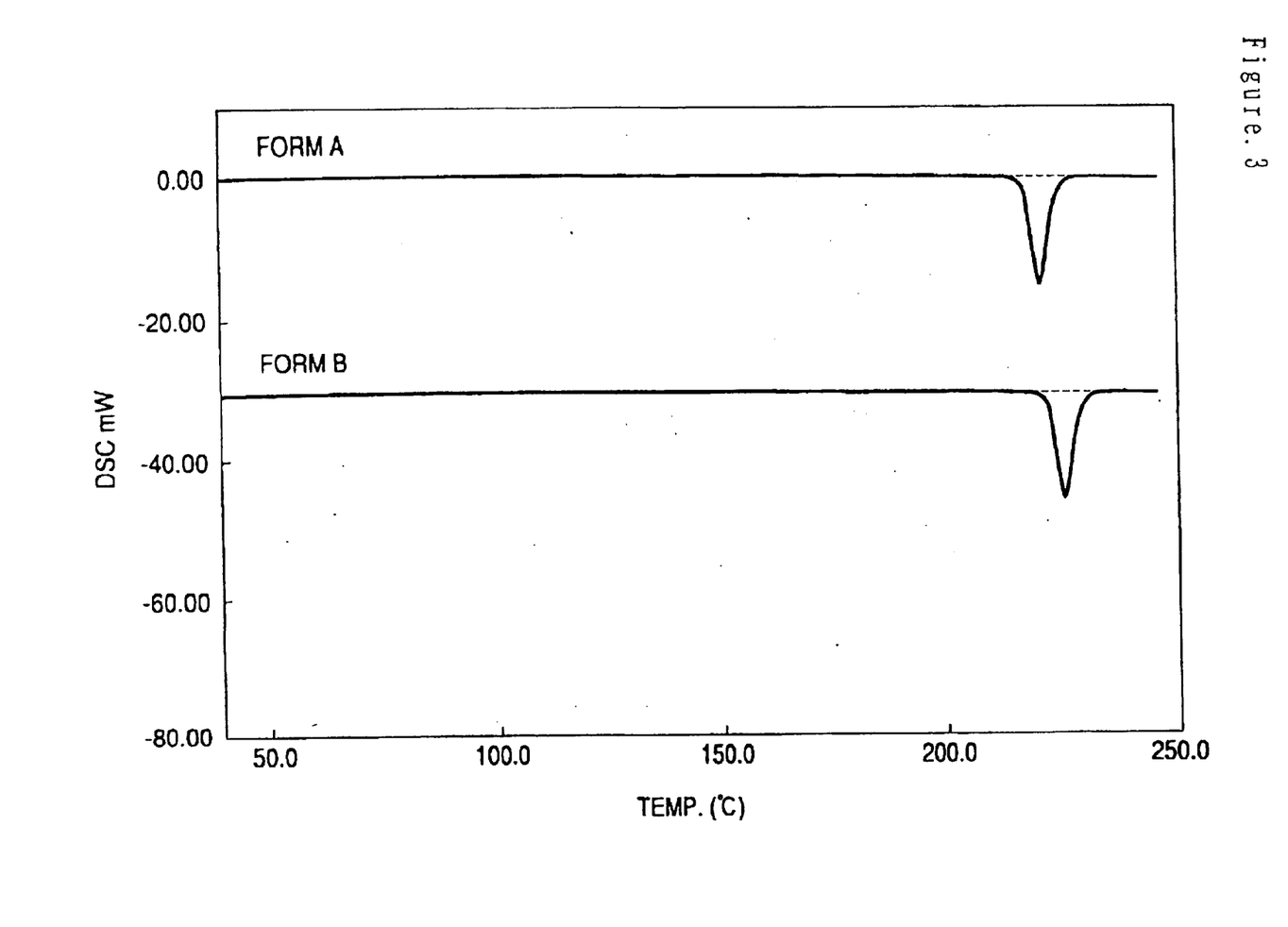
FIG. 3 shows differential scanning calorimetry (DSC) curves of the form A crystal and the form B crystal.

The differential scanning calorimetry curves of the form A crystal and the form B crystal are shown in FIG. 3. The melting point (extrapolated onset) of the form A crystal was 490.7 K (217.6° C.), and the heat of melting was 37.7 kJ/mol. The melting point (extrapolated onset) of the form B crystal was 495.7 K (about 222.6° C.), and the heat of melting was 34.0 kJ/mol.

Example 9

Form A and Form B Crystal Stability and Solubility Characteristics

Saturated solutions of the form A crystals and the form B crystals were prepared at room temperature (25° C.). The concentrations of N-(2,3-dimethyl-5,6,7,8-tetrahydrofuro[2,3-b]quinolin-4-yl)-2-(2-oxopyrrolidin-1-yl)acetamide in each of the saturated solutions then was measured to obtain the water solubility of the form A and form B crystals.

About 20 mg of the form A crystal was weighed and put into separate tube with screwcap, then 10 mL of water were added, and the tube was capped. The tube was ultrasonicated for 5 minutes to suspend the sample. The tube then was shaken for 3 hours in an incubator, with the shaker setting at an appropriate temperature to obtain a saturated solution. The saturated solutions were filtrated using a Chromatodisk 25A (GL Science). 5 mL of the filtrate were measured, and 5 mL of the internal standard solutions (16 mg of isopropyl p-hydroxybenzoate were weighed, and 50% methanol was added to obtain 100 mL of an internal standard solutions) were added, and then 50% methanol was added to obtain 50 mL of sample solutions. 20 mg of each crystals were weighed, and then methanol was added to obtain 50 mL solutions. 5 mL of the aforementioned solutions were measured, and then 5 mL of the internal standard solutions were added, and then 50% of methanol was added to obtain 50 mL of the standard solutions. 10 µL of each sample solution and the standard solutions were subjected to liquid chromatography (LC) under the following conditions, and the following calculations were carried out to obtain the saturated solubility of each crystal.

Saturated solubility (mg/mL)=Qt/Qs×Ws×1/50

Qt: A ratio of a peak area of each crystal for a peak area of the internal standard in each sample solution Qs: A ratio of a peak area of the form A crystal for a peak area of the internal standard in the standard solutions Ws: Sample (mg) of the standard sample of each crystal Conditions of LC:

LC6A Liquid Chromatograph Systems (Shimazu)

Detector: Ultraviolet spectroscopy (272 nm)

Column: L-Column (4.6×250 mm)

Column Temperature: 40° C.

Eluent: mixed solvent of methanol/0.02 M ammonium acetate (60:40)

Flow rate: 0.8 mL/minute

Figure 4:
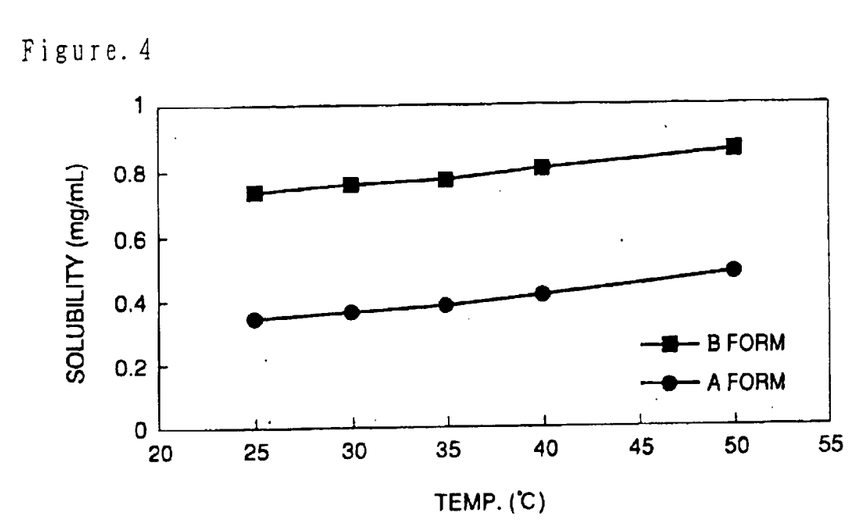
FIG. 4 shows solubility patterns of the form A crystal and the form B crystal.

The solubility pattern of each crystal is shown in FIG. 4. The solubility of the form A crystal at 25° C. is 0.35 mg/mL, and the solubility of the form B crystal at 25° C. is 0.73 mg/mL. The form A is more stable at room temperature (25° C.) than the form B crystal, while the solubility of the form B crystal is higher than the solubility of the form A crystal at 25° C. and over a relatively wide temperature range.

Industrial Applicability

The form A crystal and the form B crystal of the present invention can be prepared with good reproducibility by using solvents safe for human bodies (e.g., pharmaceutically, pharmacologically, and/or physiologically acceptable). Therefore, it is far more useful as a pharmaceutical bulk or an active ingredient of a medicament. Furthermore, the form A crystal is extremely stable in wide temperature including room temperature and also has good stability during storage. The form B crystal has good solubility.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A polymorph A crystal of N-(2,3-dimethyl-5,6,7,8-tetrahydrofuro[2,3-b]quinolin-4-yl)-2-(2-oxopyrrolidine-1-yl)acetamide characterized at least one of the following:

(a) a melting point (extrapolated onset) obtained from a differential scanning calorimetry curve lower than 220° C., (b) at least one peak in the X-ray diffraction spectrum at diffraction angle, 2θ, of 8.7°, 9.8°, 11.4°, 13.3°, 15.5°, 16.8°, and/or 17.6° (±0.2°, respectively), (c) the absence of a peak at X-ray diffraction angle, 2θ, of 7.3°, 9.3°, 11.9°, and/or 14.8° (±0.2°, respectively), and/or (d) a water solubility (at 25° C.) of lower than 0.5 mg/mL.

2. The polymorph A crystal of claim 1 having a melting point (extrapolated onset) obtained from a differential scanning calorimetry curve lower than 220° C.

3. The polymorph A crystal of claim 2 having a melting point (extrapolated onset) obtained from a differential scanning calorimetry curve of about 213–220° C.

4. The polymorph A crystal of claim 3 having a melting point (extrapolated onset) obtained from a differential scanning calorimetry curve of about 217.6° C.

5. The polymorph A crystal of claim 1 having at least one peak in the X-ray diffraction spectrum at diffraction angle, 2θ, of 8.7°, 9.8°, 11.4°, 13.3°,15.5°, 16.8°, and/or 17.6° (±0.2°, respectively).

6. The polymorph A crystal of claim 5 having a peak in the X-ray diffraction spectrum at diffraction angle, 2θ, of 9.8° (±0.2°).

7. The polymorph A crystal of claim 6 having peaks in the X-ray diffraction spectrum at diffraction angles, 2θ, of 8.7°and 16.8° (±0.2°, respectively).

8. The polymorph A crystal of claim 7 having peaks in the X-ray diffraction spectrum at diffraction angles, 2θ, of 11.4°, 13.3°, and 15.5° (±0.2°, respectively).

9. The polymorph A crystal of claim 8 having a peak in the X-ray diffraction spectrum at diffraction angle, 2θ, of 17.6° (±0.2°).

10. The polymorph A crystal of claim 1 having the absence of a peak at X-ray diffraction angle, 2θ, of 7.3°, 9.3°, 11.9°, and/or 14.8° (±0.2°, respectively).

11. The polymorph A crystal of claim 10 having the absence of a peak at X-ray diffraction angle, 2θ, of 7.3° (±0.2°).

12. The polymorph A crystal of claim 11 having the absence of a peak at X-ray diffraction angle, 2θ, of 9.3° (±0.2°).

13. The polymorph A crystal of claim 12 having the absence of a peak at X-ray diffraction angles, 2θ, of 11.9° and 14.8° (±0.2°, respectively).

14. The polymorph A crystal of claim 1 having a water solubility (at 25° C.) of lower than 0.5 mg/mL.

15. The polymorph A crystal of claim 14 having a water solubility (at 25° C.) in the range of about 0.1–0.5 mg/mL.

16. The polymorph A crystal of claim 15 having a water solubility (at 25° C.) of about 0.35 mg/mL.

17. A polymorph A crystal of N-(2,3-dimethyl-5,6,7,8-tetrahydrofuro[2,3-b]quinolin-4-yl)-2-(2-oxopyrrolidine-1-yl)acetamide having
   (a) a melting point (extrapolated onset) obtained from a differential scanning calorimetry curve lower than 220° C.,
   (b) an X-ray diffraction spectrum at diffraction angle, 2θ, having one or more peaks selected from the group consisting of 8.7°, 9.8°, 11.4°, 13.3°, 15.5°, 16.8°, and/or 17.6° (±0.2°, respectively); said X-ray diffraction spectrum having the absence of peaks at diffraction angle, 2θ, selected from the group consisting of 7.3°, 9.3°, 11.9°, and/or 14.8° (±0.2°, respectively), and
   (c) a water solubility (at 25° C.) of lower than 0.5 mg/mL.

18. A polymorph A crystal of N-(2,3-dimethyl-5,6,7,8-tetrahydrofuro[2,3-b]quinolin-4-yl)-2-(2-oxopyrrolidine-1-yl)acetamide having the X-ray diffraction spectrum substantially consistent with diffraction angle in the X-ray diffraction spectrum of FIG. 1-a.

19. A polymorph A crystal of N-(2,3-dimethyl-5,6,7,8-tetrahydrofuro[2,3-b]quinolin-4-yl)-2-(2oxopyrrolidine-1-yl)acetamide having the differential scanning calorimetry curve substantially consistent with the differential scanning calorimetry curve of FIG. 3.

20. A polymorph B crystal of N-(2,3-dimethyl-5,6,7,8-tetrahydrofuro[2,3-b]quinolin-4-yl)-2-2-oxopyrrolidine-1-yl)acetamide having at least one of the following:
   (a) a melting point (extrapolated onset) obtained from a differential scanning calorimetry curve higher than 220° C.,
   (b) at least one peak in the X-ray diffraction spectrum at diffraction angle, 2θ, of 7.3°, 9.3°, 11.9°, 13.5°, 14.8°, 15.9°, 17.5°, and/or 18.6° (±0.2°, respectively),
   (c) the absence of a peak at X-ray diffraction angle, 2θ, of 8.7°, 9.8°, and/or 16.8° (±0.2°, respectively), and/or
   (d) a water solubility (at 25° C.) of higher than 0.5 mg/mL.

21. The polymorph B crystal of claim 20 having a melting point (extrapolated onset) obtained from a differential scanning calorimetry curve higher than 220° C.

22. The polymorph B crystal of claim 21 having a melting point (extrapolated onset) obtained from a differential scanning calorimetry curve of about 220–225° C.

23. The polymorph B crystal of claim 22 having a melting point (extrapolated onset) obtained from a differential scanning calorimetry curve of about 222.6° C.

24. The polymorph B crystal of claim 20 having at least one peak in the X-ray diffraction spectrum at diffraction angle, 2θ, of 7.3°, 9.3°, 11.9°, 13.5°, 14.8°, 15.9°, 17.5°, and/or 18.6° (±0.2°, respectively).

25. The polymorph B crystal of claim 24 having a peak in the X-ray diffraction spectrum at diffraction angle, 2θ, of 7.3° (±0.2°).

26. The polymorph B crystal of claim 25 having peaks in the X-ray diffraction spectrum at diffraction angles, 2θ, of 9.3°and 11.9° (±0.2°, respectively).

27. The polymorph B crystal of claim 26 having a peak in the X-ray diffraction spectrum at diffraction angle, 2θ, of 14.8° (±0.2°).

28. The polymorph B crystal of claim 27 having peaks in the X-ray diffraction spectrum at diffraction angles, 2θ, of 13.5°, 15.9, 17.5°, and 18.6° (±0.2°, respectively).

29. The polymorph B crystal of claim 20 having the absence of a peak at X-ray diffraction angle, 2θ, of 8.7°, 9.8°, and/or 16.8° (±0.2°, respectively).

30. The polymorph B crystal of claim 29 having the absence of a peak at X-ray diffraction angle, 2θ, of 9.8° (±0.2°).

31. The polymorph B crystal of claim 30 having the absence of a peak at X-ray diffraction angle, 2θ, of 8.7° (±0.2°).

32. The polymorph B crystal of claim 31 having the absence of a peak at X-ray diffraction angle, 2θ, of 16.8° (±0.2°).

33. The polymorph B crystal of claim 20 having a water solubility (at 25° C.) of higher than 0.5 mg/mL.

34. The polymorph B crystal of claim 33 having a water solubility (at 25° C.) in the range of about 0.5–1 mg/mL.

35. The polymorph B crystal of claim 34 having a water solubility (at 25° C.) of about 0.73 mg/mL.

36. A polymorph B crystal of N-(2,3-dimethyl-5,6,7,8-tetrahydrofuro[2,3-b]quinolin-4-yl)-2-(2-oxopyrrolidin-1-yl)acetamide having
   (a) a melting point (extrapolated onset) obtained from a differential scanning calorimetry curve higher than 220° C.,
   (b) an X-ray diffraction spectrum at diffraction angle, 2θ, having one or more peaks selected from the group consisting of 7.3°, 9.3°, 11.9°, 13.5°, 14.8°, 15.9°, 17.5°, and/or 18.6° (±0.2°, respectively); said X-ray diffraction spectrum having the absence of peaks at diffraction angle, 2θ, selected from the group consisting of 8.7°, 9.8°, and/or 16.8° (±0.2°, respectively), and (c) a water solubility (at 25° C.) of higher than 0.5 mg/mL.

37. A polymorph B crystal of N-(2,3-dimethyl-5,6,7,8-tetrahydrofuro[2,3-b]quinolin-4-yl)-2-(2oxopyrrolidine1-yl)acetamide having the X-ray diffraction spectrum substantially consistent with diffraction angle in the X-ray diffraction spectrum of FIG. 1-b.

38. A polymorph B crystal of N-(2,3-dimethyl-5,6,7,8-tetrahydrofuro[2,3-b]quinolin-4-yl)-2-(2oxopyrrolidine-1-yl)acetamide having the differential scanning calorimetry curve substantially consistent with the differential scanning calorimetry curve of FIG. 3.

39. A pharmaceutical bulk comprising the polymorph A crystal of claim 1.

40. A pharmaceutical bulk comprising the polymorph B crystal of claim 20.

41. A pharmaceutical composition comprising a pharmaceutically acceptable carrier and the polymorph A crystal of claim 1.

42. A pharmaceutical composition comprising a pharmaceutically acceptable carrier and the polymorph B crystal of claim 20.

43. A method of treating a mammal comprising administering the pharmaceutical composition of claim 41 to the mammal to treat a disease having a malfunctioned cholinergic neuron in the mammal, wherein the disease is senile dementia.

44. A method of treating a mammal comprising administering the pharmaceutical composition of claim 41 to the mammal to treat a disease having a malfunctioned cholinergic neuron in the mammal, wherein the disease is dementia caused by Alzheimer's disease.

45. A method of treating a mammal comprising administering the pharmaceutical composition of claim 42 to the mammal to treat a disease having a malfunctioned cholinergic neuron in the mammal, wherein the disease is senile dementia.

46. A method of treating a mammal comprising administering the pharmaceutical composition of claim 42 to the mammal to treat a disease having a malfunctioned cholinergic neuron in the mammal, wherein the disease is dementia caused by Alzheimer's disease.

47. A method for preparing a polymorph A crystal or a polymorph B crystal of N-(2,3-dimethyl-5,6,7,8-tetrahydrofuro[2,3-b]quinolin-4-yl)-2-(2oxopyrrolidin-1-yl) acetamide comprising crystallizing N-(2,3-dimethyl-5,6,7,8-tetrahydrofuro[2,3-b]quinolin-4-yl)-2-(2-oxopyrrolidin-1-yl) acetamide from a physiologically compatible solvent.

48. The method of claim 47, wherein the crystal is a polymorph A crystal.

49. The method of claim 47, wherein the crystal is a polymorph B crystal.

50. The method of claim 47, wherein the solvent is selected from the group consisting of water, acetic acid, acetone, anisole, 1-butanol, 2-butanol, butyl acetate, tert-butyl methyl ether, cumene, dimethyl sulfoxide, ethanol, ethyl acetate, diethyl ether, ethyl formate, formic acid, heptane, isobuthyl acetate, isopropyl acetate, methyl acetate, 3-methyl-1-butanol, methyl ethyl ketone, methyl isobuthyl ketone, 2-methyl-1-propanol, pentane, 1-pentanol, 1-propanol, 2-propanol, propyl acetate, and combinations thereof.

51. The method of claim 47, wherein the solvent is ethanol and/or water.

52. A method for preparing the polymorph A crystal of N-(2,3-dimethyl-5,6,7,8-tetrahydrofuro[2,3b]quinolin-4-yl)-2-(2-oxopyrrolidin-1-yl) acetamide comprising preparing N-(2,3-dimethyl-5,6,7,8-tetrahydrofuro[2,3b]quinolin-4-yl)-2-(2-oxopyrrolidin-1-yl)acetamide from a solution where the supersaturability is less than about 5.

53. The method of claim 52 including the step of recrystallizing slowly, wherein the precise time frame depends on the scale of the reaction, from several hours to several days.

54. The method of claims 52 including the step of converting the polymorph B crystals of N-(2,3-dimethyl-5,6,7,8-tetrahydrofuro[2,3b]quinolin-4-yl)-2-(2-oxopyrrolidin-1-yl)acetamide into the form A crystals of N-(2,3-dimethyl-5,6,7,8-tetrahydrofuro[2,3-b]quinolin-4-yl)-2-(2-oxopyrrolidin-1-yl)acetamide by stirring the suspension slowly, wherein the precise time frame depends on scale of the reaction, from several hours to several days.

55. A method for preparing the polymorph B crystal of N-(2,3-dimethyl-5,6,7,8-tetrahydrofuro[2,3-b]quinolin-4-yl)-2-(2-oxopyrrolidin-1-yl)acetamide comprising preparing N-(2,3-dimethyl-5,6,7,8-tetrahydrofuro[2,3-b]quinolin-4-yl)-2-(2-oxopyrrolidin-1-yl)acetamide from a solution where the supersaturability is more than about 20.

56. The method of claim 55, wherein the solution of N-(2,3-dimethyl-5,6,7,8-tetrahydrofuro[2,3-b]quinolin-4-yl)-2-(2-oxopyrrolidin-1-yl)acetamide is dissolved as a crude crystal in a solvent, with heating, followed by cooling to a temperature less than 25° C.

* * * * *

UNITED STATES PATENT AND TRADEMARK OFFICE
CERTIFICATE OF CORRECTION

PATENT NO. : 6,884,805 B2
DATED : April 26, 2005
INVENTOR(S) : Yamabe et al.

It is certified that error appears in the above-identified patent and that said Letters Patent is hereby corrected as shown below:

Column 12,
Line 53, "oxopyrrolidine" should read -- oxopyrrolidin --.
Line 54, "characterized" should read -- having --.

Column 13,
Lines 42 and 56, "oxopyrrolidine" should read -- oxopyrrolidin --.
Line 61, "2oxopyrrolidine" should read -- 2-oxopyrrolidin --.
Line 66, "2-oxopyrrolidine" should read -- (2-oxopyrrolidin --.

Column 14,
Line 35, "15.9" should read -- 15.9° --.

Column 15,
Lines 4 and 9, "2oxopyrrolidine" should read -- 2-oxopyrrolidin --.
Line 45, "2oxopyrrolidin" should read -- 2-oxopyrrolidin --.

Column 16,
Lines 19, 21 and 29, "[2,3b]" should read -- [2,3-b] --.
Line 27, "claims" should read -- claim --.

Signed and Sealed this

Twenty-third Day of August, 2005

JON W. DUDAS
*Director of the United States Patent and Trademark Office*